US011326988B2

(12) United States Patent
Abe

(10) Patent No.: US 11,326,988 B2
(45) Date of Patent: May 10, 2022

(54) SENSOR MODULE FOR DETECTING A COMPONENT IN A SAMPLE FLUID AND METHOD FOR DETECTING A COMPONENT IN A SAMPLE FLUID

(71) Applicant: KYOCERA Corporation, Kyoto (JP)

(72) Inventor: Shinichi Abe, Uji (JP)

(73) Assignee: KYOCERA Corporation, Kyoto (JP)

( * ) Notice: Subject to any disclaimer, the term of this patent is extended or adjusted under 35 U.S.C. 154(b) by 1 day.

(21) Appl. No.: 16/336,267

(22) PCT Filed: Sep. 29, 2017

(86) PCT No.: PCT/JP2017/035534
§ 371 (c)(1),
(2) Date: Mar. 25, 2019

(87) PCT Pub. No.: WO2018/062503
PCT Pub. Date: Apr. 5, 2018

(65) Prior Publication Data
US 2019/0250077 A1    Aug. 15, 2019

(30) Foreign Application Priority Data

Sep. 30, 2016 (JP) .............................. JP2016-194409

(51) Int. Cl.
*G01N 1/22* (2006.01)
*G01N 27/12* (2006.01)
(Continued)

(52) U.S. Cl.
CPC ......... *G01N 1/2205* (2013.01); *G01N 1/2247* (2013.01); *G01N 19/00* (2013.01);
(Continued)

(58) Field of Classification Search
CPC .... G01N 1/2205; G01N 1/2247; G01N 27/12; G01N 30/34; G01N 33/0022;
(Continued)

(56) References Cited

U.S. PATENT DOCUMENTS

| 4,619,136 A * | 10/1986 | Ortiz ...................... G01N 15/08 73/38 |
| 7,998,252 B2 * | 8/2011 | Huza .................. B01D 46/0028 95/278 |

(Continued)

FOREIGN PATENT DOCUMENTS

| CN | 103649738 A | 3/2014 |
| JP | H11174051 A | 7/1999 |

(Continued)

OTHER PUBLICATIONS

Inagawa Nobuhiro, "Vacuum desorption type VOC recovery technology using silica gel", Adsorption News, Jan. 30, 2013, pp. 5-11, vol. 26, No. 4, The Japan Society on Absorption, Japan, ISSN 0917-9917.

*Primary Examiner* — Tran M. Tran
(74) *Attorney, Agent, or Firm* — Studebaker & Brackett PC

(57) ABSTRACT

A sensor module includes a sensor that detects a first component, a first flow channel to supply a sample fluid to the sensor, and a second flow channel to supply a reference fluid to the sensor. The reference fluid includes a second component different from the first component included in the sample fluid. The second flow channel includes a first filter that reduces the amount of the first component in the reference fluid.

11 Claims, 7 Drawing Sheets

(51) Int. Cl.
*G01N 33/00* (2006.01)
*G01N 19/00* (2006.01)
*G01N 30/34* (2006.01)
*G01N 1/34* (2006.01)

(52) U.S. Cl.
CPC .............. *G01N 27/12* (2013.01); *G01N 30/34* (2013.01); *G01N 33/0009* (2013.01); *G01N 1/34* (2013.01)

(58) Field of Classification Search
CPC ........... G01N 33/0014; G01N 33/0021; G01N 33/0059; G01N 33/006; G01N 33/0009; G01N 2033/0072; G01N 33/4972; G01N 2015/084; G01N 33/0067
USPC ................................................ 73/23.2–31.07
See application file for complete search history.

(56) References Cited

U.S. PATENT DOCUMENTS

| | | | | |
|---|---|---|---|---|
| 8,261,540 | B2 * | 9/2012 | Konstandopoulos | F01N 3/021 55/282.2 |
| 8,485,031 | B2 * | 7/2013 | Speldrich | G01F 1/40 73/204.22 |
| 8,584,509 | B2 * | 11/2013 | Groves | G01N 27/66 436/126 |
| 8,627,710 | B2 * | 1/2014 | Nylander | G01N 33/0009 73/40.7 |
| 8,881,600 | B2 * | 11/2014 | Puppini | A61M 1/165 73/861 |
| 8,910,506 | B2 * | 12/2014 | Johnson | G01F 1/05 73/23.2 |
| 9,360,411 | B2 * | 6/2016 | Woolard | G01M 3/04 |
| 9,366,615 | B2 * | 6/2016 | Puppini | A61M 1/34 |
| 9,377,380 | B2 * | 6/2016 | Groves | G01N 27/66 |
| 9,417,207 | B2 * | 8/2016 | Marra | G01N 1/2273 |
| 9,689,864 | B2 * | 6/2017 | Ahmad | G01N 33/52 |
| 9,702,802 | B2 * | 7/2017 | Ajay | G01N 1/2205 |
| 9,726,591 | B2 * | 8/2017 | Helle | A61L 2/022 |
| 9,797,815 | B2 * | 10/2017 | Cooper | A61B 5/082 |
| 10,054,575 | B2 * | 8/2018 | Refai-Ahmed | G01N 33/0016 |
| 11,016,014 | B2 * | 5/2021 | Odling | B01D 46/0086 |
| 2010/0262034 | A1 * | 10/2010 | Kawata | G01N 30/6095 600/532 |
| 2018/0321206 | A1 * | 11/2018 | Chen | G01N 33/0022 |
| 2021/0060473 | A1 * | 3/2021 | Caesar | B01D 46/0086 |

FOREIGN PATENT DOCUMENTS

| | | |
|---|---|---|
| JP | 2005049287 A | 2/2005 |
| JP | 2006220544 A | 8/2006 |
| JP | 2010249556 A | 11/2010 |

* cited by examiner

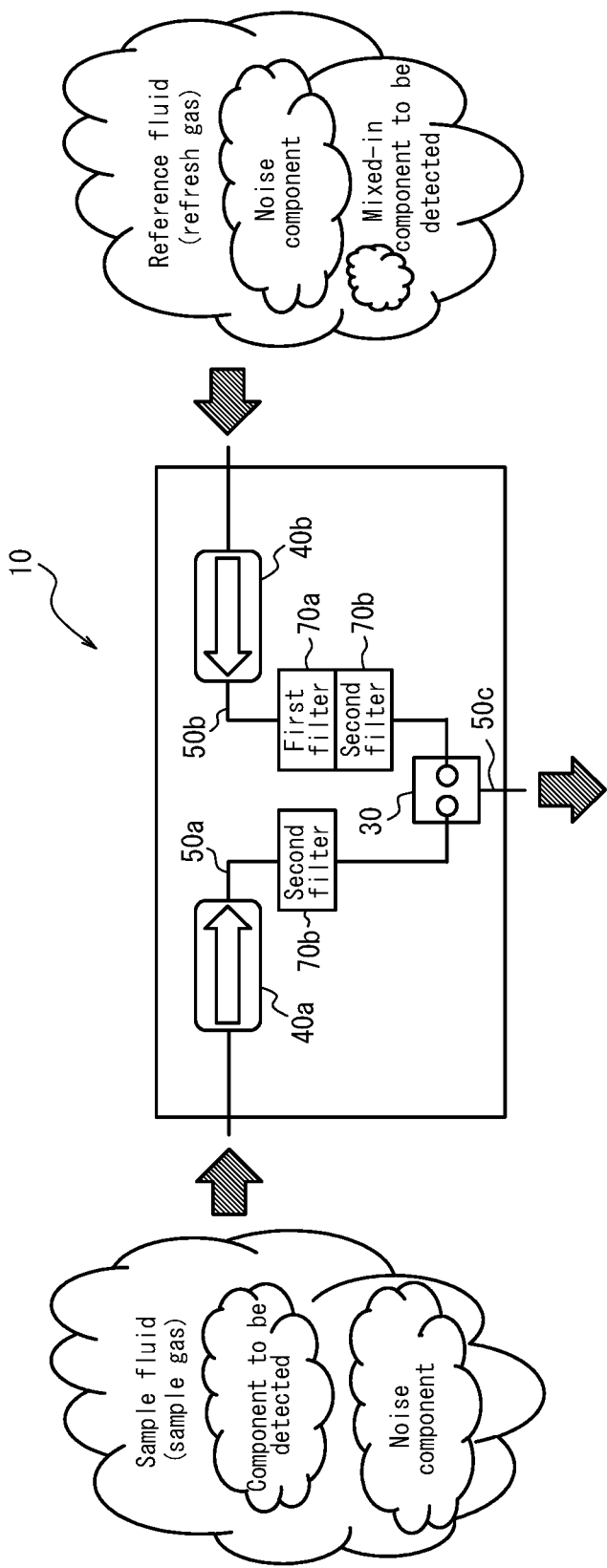

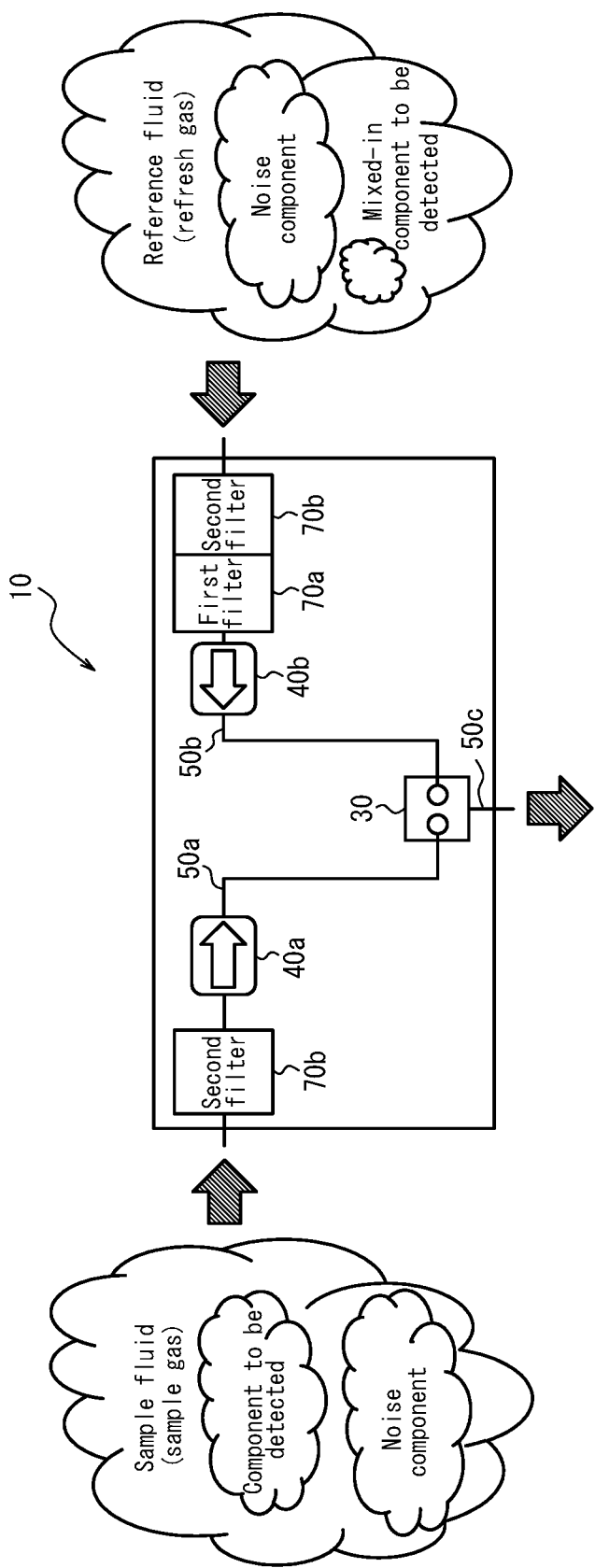

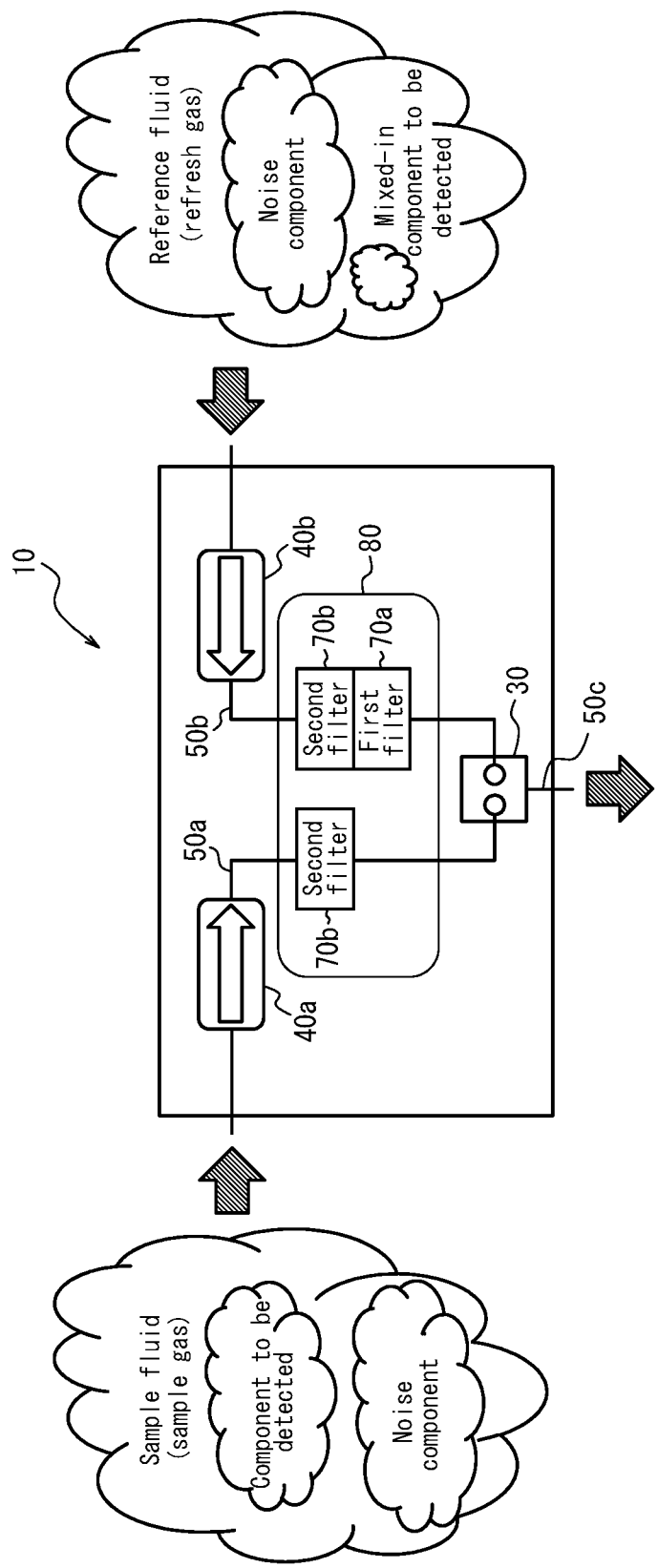

SENSOR MODULE FOR DETECTING A COMPONENT IN A SAMPLE FLUID AND METHOD FOR DETECTING A COMPONENT IN A SAMPLE FLUID

CROSS-REFERENCE TO RELATED APPLICATION

The present application claims priority to and the benefit of Japanese Patent Application No. 2016-194409 filed Sep. 30, 2016, the entire contents of which are incorporated herein by reference.

TECHNICAL FIELD

The present disclosure relates to a sensor module and a detection method.

BACKGROUND

A known sensor module detects a specific substance in a fluid. In one example, a gas component detection apparatus includes a gas inlet and a gas detector.

CITATION LIST

Patent Literature

PTL 1: JP2010249556A

SUMMARY

A sensor module according to an embodiment of the present disclosure includes a sensor configured to detect a first component, a first flow channel configured to supply a sample fluid to the sensor, and a second flow channel configured to supply a reference fluid to the sensor. The reference fluid includes a second component that is included in the sample fluid and differs from the first component. The second flow channel includes a first filter configured to reduce the amount of the first component in the reference fluid.

A detection method according to an embodiment of the present disclosure is performed using a sensor module including a first supply unit provided in a first flow channel, a second supply unit provided in a second flow channel including a second filter configured to reduce an amount of a first component, and a sensor. The detection method includes driving the first supply unit to supply a sample fluid to the sensor through the first flow channel, driving the second supply unit to supply a reference fluid to the sensor through the second flow channel, the reference fluid including a second component that is included in the sample fluid and differs from the first component, and detecting the first component with the sensor.

BRIEF DESCRIPTION OF THE DRAWINGS

In the accompanying drawings:

FIG. 5 illustrates a modification to the sensor module;

FIG. 6 illustrates a modification to the sensor module; and

FIG. 7 illustrates a modification to the sensor module.

DETAILED DESCRIPTION

Embodiments of the present disclosure are now described with reference to the drawings.

Figure 1:
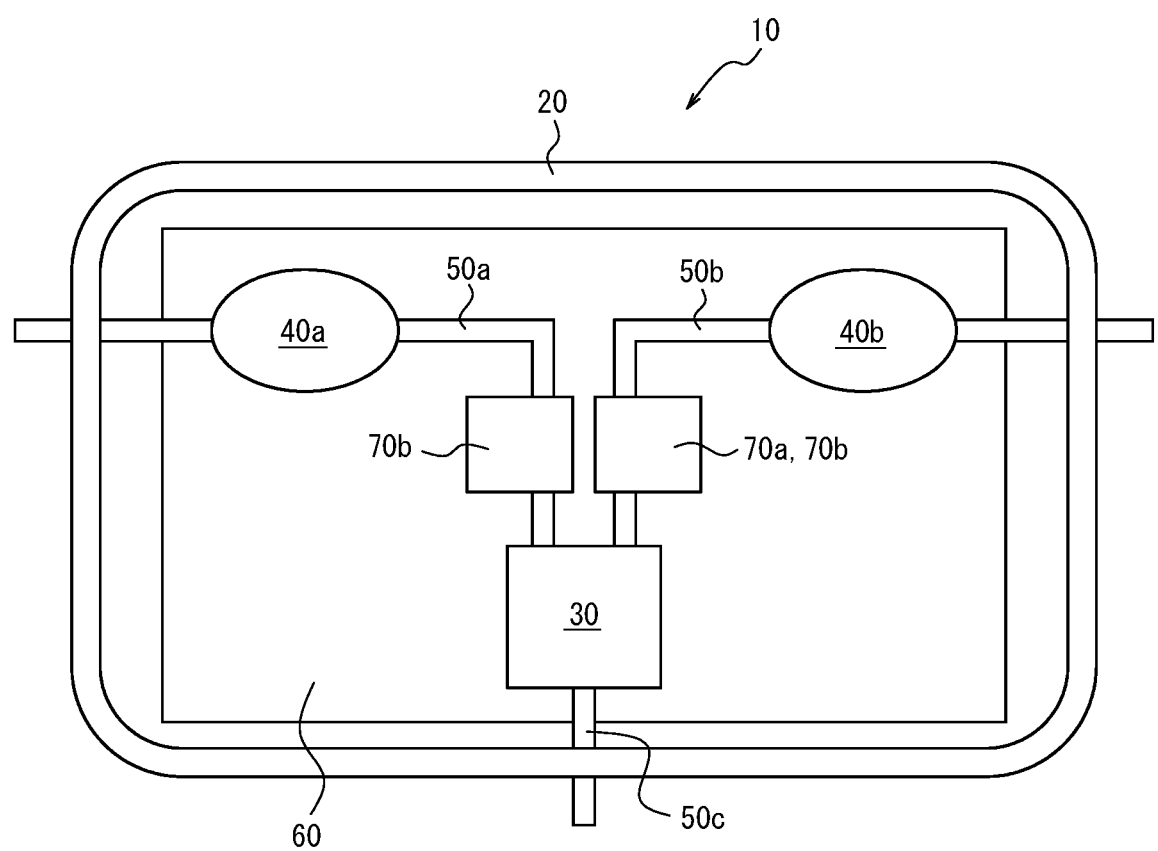
FIG. 1 is a conceptual diagram of a sensor module according to an embodiment of the present disclosure.

FIG. 1 is a conceptual diagram of a sensor module 10 according to an embodiment of the present disclosure. The sensor module 10 includes a housing 20, for example. For the sake of illustration, the inside of the housing 20 is illustrated in FIG. 1 with the surface of a portion of the housing 20 removed. On the basis of a fluid to be inspected (sample fluid) and a fluid serving as a comparison (reference fluid), the sensor module 10 calculates the concentration of a component to be detected, which is a first component included in the sample fluid.

Inside the housing 20, the sensor module 10 includes a chamber 30, a first supply unit 40a, a second supply unit 40b, a first flow channel 50a, a second flow channel 50b, a third flow channel 50c, and an electronic circuit board (board) 60.

The chamber 30 includes a sensor therein. The first flow channel 50a, the second flow channel 50b, and the third flow channel 50c are connected in the chamber 30. Fluids are supplied to the chamber 30 from the first flow channel 50a and the second flow channel 50b. The chamber 30 discharges the fluids from the third flow channel 50c. The sensor inside the chamber 30 includes a plurality of reactive portions. The reactive portions are, for example, films. The reactive portions react to specific components. At least one of the reactive portions reacts to the component to be detected. In other words, at least one of the reactive portions detects the component to be detected. The reactive portions deform by adsorbing a specific component included in a fluid. The reactive portions may, for example, be made of material such as polystyrene, chloroprene rubber, polymethyl methacrylate, or nitrocellulose. The reactive portions output an electric signal corresponding to the reaction to a specific component. The signal is, for example, outputted as a voltage.

The first supply unit 40a is attached to the first flow channel 50a, and the second supply unit 40b is attached to the second flow channel 50b. The first supply unit 40a supplies the sample fluid and the second supply unit 40b supplies the reference fluid to the chamber 30. The first supply unit 40a and the second supply unit 40b are, for example, each formed by a piezoelectric pump.

The first flow channel 50a and the second flow channel 50b are, for example, formed by tubular members. The sample fluid is supplied to the chamber 30 through the first flow channel 50a. The reference fluid is supplied to the chamber 30 through the second flow channel 50b. The first flow channel 50a and the second flow channel 50b each include a filter. Details of the filter included in the first flow channel 50a and the second flow channel 50b are provided below.

The third flow channel 50c is, for example, formed by a tubular member. The fluid supplied to the chamber 30 is discharged from the third flow channel 50c.

The board 60 implements a controller, a storage, and the like of the sensor module 10, described below.

Figure 2:
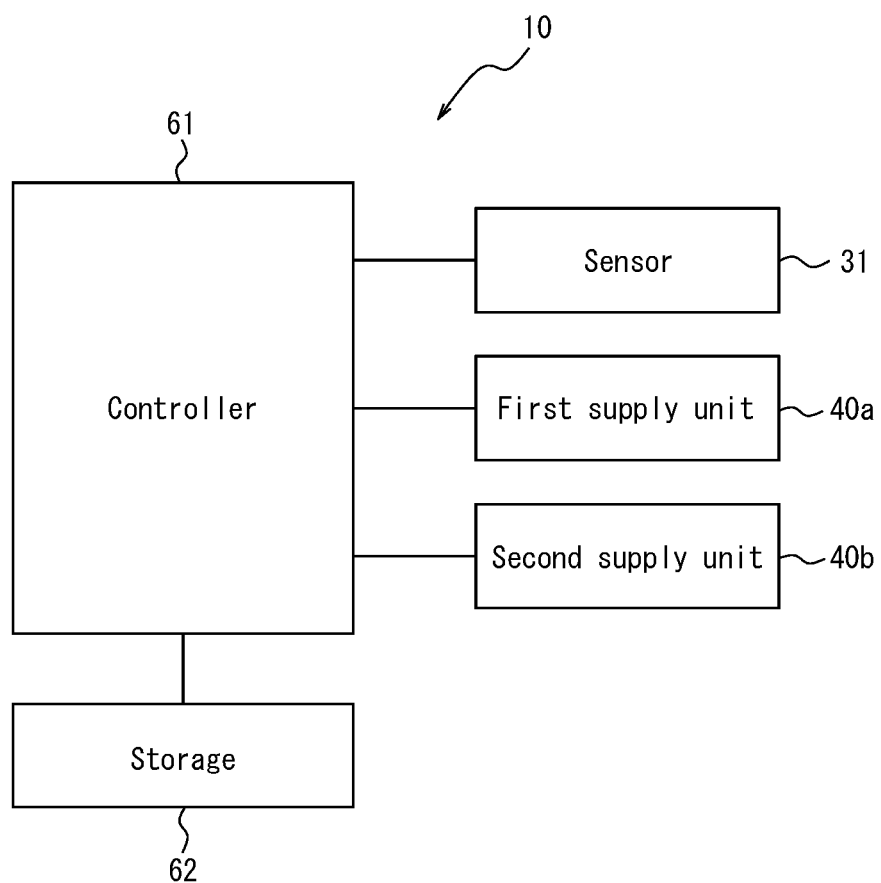
FIG. 2 is a functional block diagram illustrating the schematic configuration of the sensor module in FIG. 1.

FIG. 2 is a functional block diagram illustrating the schematic configuration of the sensor module 10 in FIG. 1.

The sensor module 10 in FIG. 2 includes a controller 61, a storage 62, a sensor 31, the first supply unit 40a, and the second supply unit 40b.

The sensor 31 is provided inside the chamber 30, as described above. The sensor 31 supplies the signal output from each reactive portion to the controller 61.

The first supply unit 40a supplies the fluid from the first flow channel 50a, and the second supply unit 40b supplies the fluid from the second flow channel 50b, to the chamber 30 at predetermined times in response to control by the controller 61.

The controller 61 is a processor that controls and manages the sensor module 10 overall, starting with the functional blocks of the sensor module 10. The controller 61 is a processor, such as a central processing unit (CPU), that executes a program with prescribed control procedures. Such a program may, for example, be stored in the storage 62, on an external storage medium connected to the sensor module 10, or the like.

The controller 61 calculates the concentration of the component to be detected in the sample fluid on the basis of the signal outputted from the sensor 31. Details of how the controller 61 controls the first supply unit 40a and the second supply unit 40b and calculates the concentration of the component to be detected are described below.

The storage 62 may, for example, be a semiconductor memory, a magnetic memory, or the like. The storage 62 stores various information and/or programs for operating the sensor module 10. The storage 62 may also function as a working memory.

Figure 3:
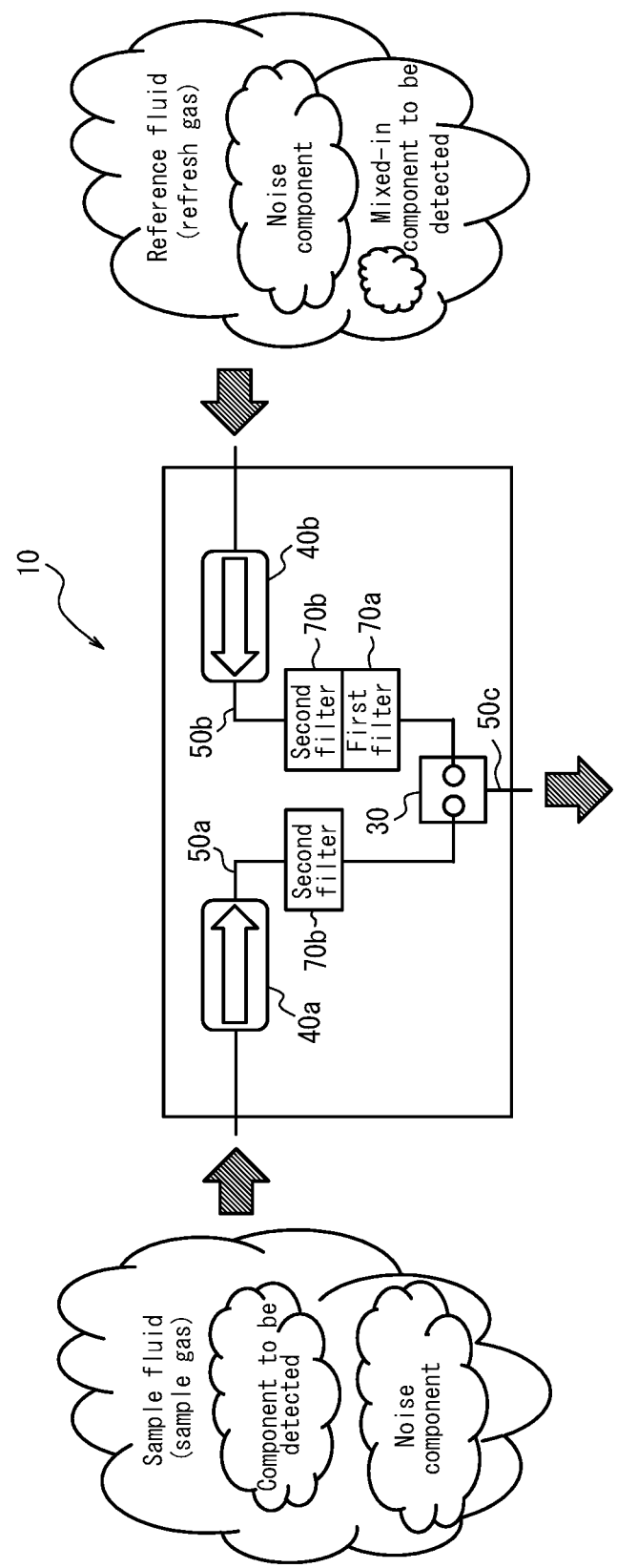
FIG. 3 schematically illustrates the flow of fluid in the sensor module in FIG. 1.

Next, details regarding the control of the first supply unit 40a and the second supply unit 40b and calculation of the concentration of the component to be detected by the controller 61 are described. FIG. 3 schematically illustrates the flow of fluid in the sensor module 10. In FIG. 3, the arrows in the first supply unit 40a and the second supply unit 40b respectively indicate the directions in which the first supply unit 40a and the second supply unit 40b channel the fluid.

The sample fluid (sample gas) is supplied to the first flow channel 50a. Here, an example of the sample fluid being human breath is described. The sample fluid is not limited to being human breath, however, and can be any fluid to be inspected. When the sample fluid is human breath, the component to be detected may, for example, be acetone, ethanol, carbon monoxide, or the like. The component to be detected is not limited to these examples, either. A noise component (noise gas) that is a second component is included in the sample fluid. The noise component is a component other than the component to be detected. All components other than the component to be detected, such as oxygen, carbon dioxide, nitrogen, water vapor, and the like, are included in the noise component.

The reference fluid (refresh gas) is supplied to the second flow channel 50b. Air, for example, can be used as the reference fluid when the sample fluid is human breath. The reference fluid is not, however, limited to air. Noise components, such as oxygen, carbon dioxide, nitrogen, water vapor, and the like, are included in the reference fluid. In some cases, the component to be detected is mixed into the reference fluid. The amount of the component to be detected mixed into the reference fluid is, for example, an extremely small amount compared to the noise component included in the reference fluid.

The second flow channel 50b includes a first filter 70a. The first filter 70a is provided in the second flow channel 50b on the chamber 30 side (downstream) from the second supply unit 40b. The first filter 70a reduces the component to be detected in the fluid. The first filter 70a is, for example, a member (adsorbent) that adsorbs the component to be detected. Activated charcoal, for example, can be used as the first filter 70a. The first filter 70a may, however, be made of a member other than activated charcoal.

The first flow channel 50a and the second flow channel 50b each include a second filter 70b. The second filter 70b is provided in the first flow channel 50a and the second flow channel 50b on the chamber 30 side (downstream) from the first supply unit 40a and the second supply unit 40b. The second filter 70b reduces the noise component in the fluid. The second filter 70b is, for example, a member (adsorbent) that adsorbs the noise component. For example, silica gel, ion exchange resin, or the like can be used as the second filter 70b. The second filter 70b may, however, be made of a member other than silica gel or ion exchange resin.

The first filter 70a may be a member that reduces the noise component more than the second filter 70b does. In the example illustrated in FIG. 3, the first filter 70a is provided in the second flow channel 50b towards the chamber 30, which includes the sensor 31, from the second filter 70b (downstream).

The controller 61 controls the first supply unit 40a and the second supply unit 40b so that the sample fluid from the first flow channel 50a and the reference fluid from the second flow channel 50b are supplied alternately to the chamber 30. In other words, the second supply unit 40b does not send the reference fluid to the chamber 30 while the first supply unit 40a is sending the sample fluid to the chamber 30. The first supply unit 40a does not send the sample fluid to the chamber 30 while the second supply unit 40b is sending the reference fluid to the chamber 30. The controller 61 switches between supplying fluid to the chamber 30 with the first supply unit 40a and the second supply unit 40b over a fixed time period, for example.

The sample fluid supplied to the first flow channel 50a of the sensor module 10 is supplied to the chamber 30 by the first supply unit 40a. When the sample fluid is supplied to the chamber 30, the sample fluid passes through the second filter 70b. At this time, the noise component included in the sample fluid is reduced by the second filter 70b. In other words, the fluid supplied to the chamber 30 from the first flow channel 50a is a fluid yielded by reducing the noise component in the sample fluid.

The reference fluid supplied to the second flow channel 50b of the sensor module 10 is supplied to the chamber 30 by the second supply unit 40b. When the reference fluid is supplied to the chamber 30, the reference fluid passes through the second filter 70b and the first filter 70a. At this time, the noise component included in the reference fluid is reduced by the second filter 70b. The component to be detected included in the reference fluid is reduced by the first filter 70a. In other words, the fluid supplied to the chamber 30 from the second flow channel 50b is a fluid yielded by reducing the noise component and the component to be detected in the reference fluid. When the amount of the component to be detected is extremely small compared to the amount of the noise component in the reference fluid, the component to be detected is further reduced by the first filter 70a. The component to be detected can therefore be considered substantially nonincluded in the fluid supplied to the chamber 30 from the second flow channel 50b, as compared to the fluid supplied to the chamber 30 from the first flow channel 50a.

When the fluid is supplied to the chamber 30, a signal corresponding to the components of the supplied fluid is outputted to the controller 61 by the sensor 31. While fluid is being supplied from the first flow channel 50a, the sensor 31 outputs a signal (first signal) corresponding to the components of the fluid yielded by reducing the noise component in the sample fluid. While fluid is being supplied from the second flow channel 50b, the sensor 31 outputs a signal (second signal) corresponding to the fluid yielded by reducing the noise component and the component to be detected in the reference fluid. The fluids supplied to the chamber 30 from the first flow channel 50a and the second flow channel 50b are similar in that the noise component is reduced by the second filter 70b in each fluid. Signals at the same level are therefore outputted from the sensor 31 with respect to this similar component. By contrast, the component to be detected is not reduced in the sample fluid but is reduced in the reference fluid by the first filter 70a. The difference between the first signal and the second signal output from the sensor 31 can therefore be considered to be the concentration of the component to be detected substantially included in the sample fluid.

The sensor module 10 according to the present disclosure includes the first filter 70a, which reduces the amount of the component to be detected in the reference fluid, in the second flow channel 50b. Fluids are therefore supplied to the chamber 30 sequentially from the first flow channel 50a that does not include the first filter 70a and the second flow channel 50b that does include the first filter 70a. Consequently, the sample fluid in which the amount of the component to be detected is not reduced and the reference fluid in which the amount of the component to be detected is reduced are supplied to the sensor 31. The sensor 31 outputs signals (first signal and second signal) corresponding to the components of the supplied fluids. The controller 61 can therefore calculate the difference between the components of the fluids sequentially supplied to the chamber 30 on the basis of the difference between the signals received from the sensor 31. By reducing the amount of the component to be detected in the reference fluid, the sensor module 10 can thus make the difference between the first signal and the second signal more accurately reflect the concentration of the component to be detected in the sample fluid, thereby improving measurement accuracy.

In the present embodiment, the first flow channel 50a and the second flow channel 50b each include the second filter 70b, which reduces the amount of the noise component. This makes it easier to align the conditions of the noise component in the fluids supplied to the chamber 30 from the first flow channel 50a and the second flow channel 50b. The sensor module 10 can therefore reduce the effect that the difference in the noise component has on the difference between the first signal and the second signal, thereby improving measurement accuracy.

In the sensor module 10 according to the present embodiment, the first filter 70a is positioned on the sensor 31 side of the second filter 70b in the second flow channel 50b. Therefore, the amount of the noise component flowing into the first filter 70a can be reduced. As the first filter 70a and the second filter 70b adsorb more of the components in the fluid, their adsorptive power decreases. Since the second filter 70b is disposed upstream from the first filter 70a along the path of the fluid, however, the amount of components adsorbable by the first filter 70a can be reduced. This makes a decrease in the noise component reduction capability of the first filter 70a less likely. The amount of the component to be detected in the fluid supplied to the chamber 30 from the second flow channel 50b can therefore be maintained in a reduced state more easily in the sensor module 10. Accordingly, the sensor module 10 can have improved measurement accuracy.

In the sensor module 10 according to the present embodiment, the first filter 70a is provided on the sensor 31 side of the second supply unit 40b in the second flow channel 50b. The second filter 70b in the sensor module 10 is provided on the sensor 31 side of the first supply unit 40a in the first flow channel 50a and on the sensor 31 side of the second supply unit 40b in the second flow channel 50b. Therefore, when the sensor module 10 is not being used, gas such as outside air does not easily act on the first filter 70a and the second filter 70b from the first supply unit 40a and the second supply unit 40b. Accordingly, adsorption by the first filter 70a and the second filter 70b of components in the fluid can more easily be prevented when the sensor module 10 is not in use, and a decrease in the noise component reduction capability of the first filter 70a and the second filter 70b is less likely.

Figure 4:
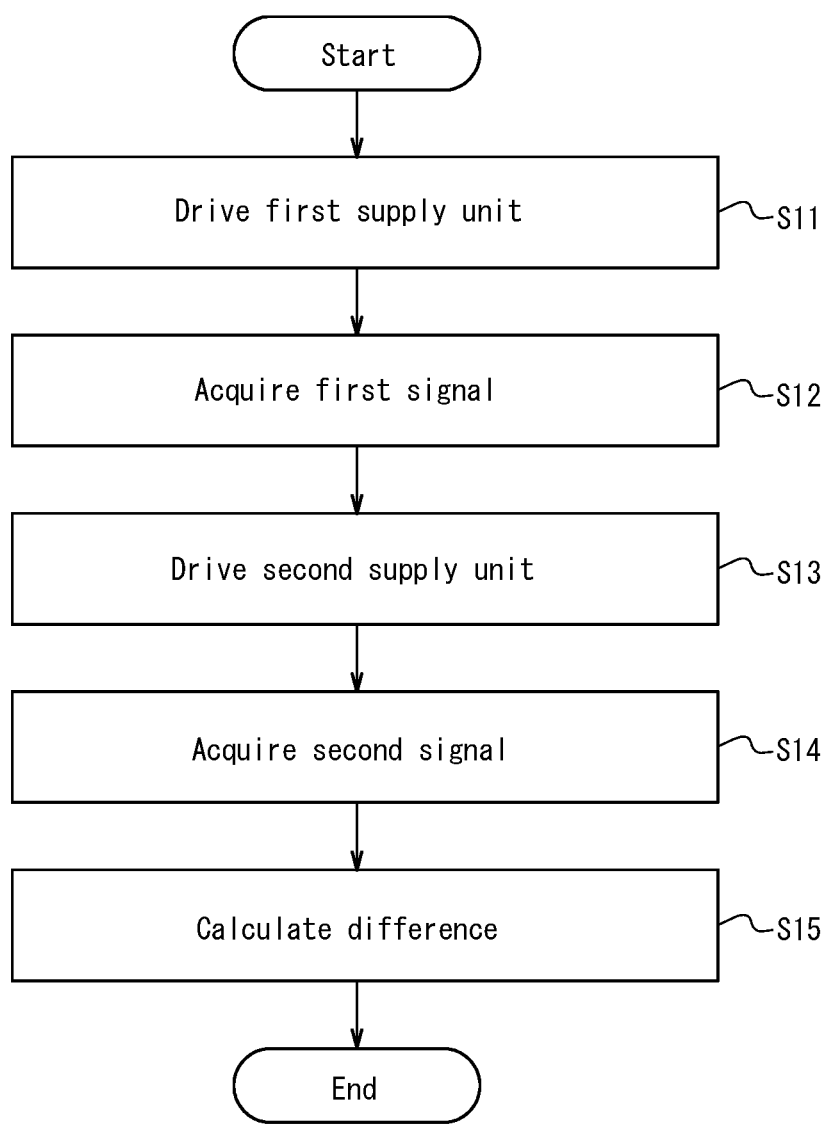
FIG. 4 is a flowchart illustrating an example of processing executed by the controller in FIG. 2.

FIG. 4 is a flowchart illustrating an example of processing executed by the controller 61 to detect a fluid component. The first supply unit 40a and the second supply unit 40b are assumed not to be driven at the point at which the processing in FIG. 4 starts.

The controller 61 drives the first supply unit 40a (step S11). The sample fluid is thus supplied to the chamber 30 from the first supply unit 40a.

When the sample fluid is supplied to the chamber 30, the sensor 31 outputs the first signal corresponding to the components of the sample fluid. The controller 61 acquires the first signal outputted from the sensor 31 (step S12).

After suspending driving of the first supply unit 40a, the controller 61 drives the second supply unit 40b (step S13). The reference fluid is thus supplied to the chamber 30 from the second supply unit 40b.

When the reference fluid is supplied to the chamber 30, the sensor 31 outputs the second signal corresponding to the components of the reference fluid. The controller 61 acquires the second signal outputted from the sensor 31 (step S14).

Execution of steps S11 and S12 and of steps S13 and S14 may be alternately repeated.

The controller 61 calculates the difference between the fluid components supplied to the chamber 30 by calculating the difference between the first signal and the second signal (step S15).

In the above embodiment, the sensor module 10 has been described as including both the first filter 70a and the second filter 70b. However, the sensor module 10 need not include the second filter 70b, for example. The sensor module 10 in this case includes the first filter 70a but not the second filter 70b in the second flow channel 50b. In this case as well, the sensor module 10 can reduce the amount of the component to be detected in the reference fluid, thereby improving the measurement accuracy for the above-described reason.

In the above embodiment, an example has been described in which the first filter 70a is positioned in the second flow channel 50b on the sensor 31 side (downstream) from the second filter 70b. The first filter 70a and the second filter 70b are not, however, limited to this arrangement. For example, as illustrated in FIG. 5, the second filter 70b may be positioned in the second flow channel 50b on the sensor 31 side (downstream) from the first filter 70a. In this arrangement as well, the first filter 70a can reduce the amount of the component to be detected in the reference fluid, thereby improving the measurement accuracy for the above-described reason.

The internal configuration of the sensor module 10 is not limited to the above embodiment. For example, as illustrated in FIG. 6, the first supply unit 40a may be provided in the first flow channel 50a on the chamber 30 side (downstream) from the second filter 70b. In other words, the second filter 70b may be provided in the first flow channel 50a on the opposite side of the first supply unit 40a from the chamber 30 (upstream). Similarly, the second supply unit 40b may be provided in the second flow channel 50b on the chamber 30 side (downstream) from the first filter 70a and the second filter 70b. In other words, the first filter 70a and the second filter 70b may be provided in the second flow channel 50b on the opposite side of the second supply unit 40b from the chamber 30 (upstream). The first filter 70a and the second filter 70b in this configuration are positioned on the opposite side of the first supply unit 40a and the second supply unit 40b from the chamber 30. This makes it easier to replace the first filter 70a and the second filter 70b when the noise component reduction capability of the first filter 70a and the second filter 70b decreases.

The sensor module 10 may, for example, include a regenerative mechanism 80, as illustrated in FIG. 7. When the capability of the first filter 70a and the second filter 70b to reduce the amount of the noise component has decreased, the regenerative mechanism 80 is capable of regenerating the capability for reduction. The regenerative mechanism 80 may, for example, regenerate the capability by heating the first filter 70a and the second filter 70b. The regenerative mechanism 80 may, for example, regenerate the capability by irradiating light onto the first filter 70a and the second filter 70b. The regenerative mechanism 80 may, for example, regenerate the capability by evacuating the first filter 70a and the second filter 70b. When the sensor module 10 includes the regenerative mechanism 80, the capability of the first filter 70a and the second filter 70b to reduce the amount of the noise component can easily be regenerated. This makes it easier to maintain the accuracy with which the sensor module 10 calculates the concentration of the component to be detected.

The regenerative mechanism 80 need not be arranged in the sensor module 10 so as to act on both the first filter 70a and the second filter 70b. For example, the regenerative mechanism 80 may be arranged so as to act on at least one of the first filter 70a and the second filter 70b.

The above-described sensor module 10 can be used for various purposes. As described in the above embodiment, the sensor module 10 can calculate the concentration of a predetermined component included in human breath when the sample fluid is human breath. The calculated concentration can, for example, be used to infer the state of a person's body. The inference of the state of a person's body may, for example, refer to the degree of progress of an illness in the body, to the person's state of health, or the like.

The sensor module 10 can, for example, be used to detect a predetermined gas component emitted from a food product. The concentration of the detected gas component can be used to infer the qualities of the food product. The qualities of the food product refer to the properties, quality, or the like of the food product. Examples include the freshness, ripeness, degree of aging, and degree of spoiling of the food product. The sensor module 10 can also be used for various other purposes, such as detecting a predetermined gas component emitted from a device.

Although the present disclosure is based on embodiments and drawings, it is to be noted that various changes and modifications will be apparent to those skilled in the art based on the present disclosure. Therefore, such changes and modifications are to be understood as included within the scope of the present disclosure. For example, the functions and the like included in the various components may be reordered in any logically consistent way. Furthermore, components may be combined into one or divided.

The invention claimed is:

1. A sensor module comprising:
   a sensor configured to detect a first component;
   a first flow channel configured to supply a sample fluid to the sensor;
   a second flow channel configured to supply a reference fluid to the sensor, the reference fluid including a second component that is included in the sample fluid and differs from the first component;
   a chamber in which the sensor is provided;
   a first supply unit provided in the first flow channel;
   a second supply unit provided in the second flow channel;
   a third flow channel configured to discharge the sample fluid and the reference fluid after passing the sensor; and
   a controller configured to control the first supply unit and the second supply unit such that the sample fluid from the first flow channel and the reference fluid from the second flow channel are supplied alternately to the chamber,
   wherein the second flow channel comprises a first filter configured to reduce an amount of the first component and the amount of the second component in the reference fluid;
   the first flow channel and the second flow channel each comprise a second filter configured to reduce an amount of the second component; and
   the controller calculates concentration of the first component in the sample fluid on the basis of difference between a signal corresponding to a fluid yielded by reducing the second component in the sample fluid and a signal corresponding to a fluid yielded by reducing the second component and the first component in the reference fluid, which are received from the sensor.

2. The sensor module of claim 1, wherein the first filter is configured to reduce the amount of the first component more than the second component.

3. The sensor module of claim 1, wherein the second filter is configured to reduce the amount of the second component more than the first component.

4. The sensor module of claim 1, wherein the first filter is configured to reduce the amount of the first component more than the second filter.

5. The sensor module of claim 1, wherein the first filter is positioned downstream from the second filter in the second flow channel.

6. The sensor module of claim 1, further comprising a supply unit, in the second flow channel upstream from the first filter, configured to supply the reference fluid to the sensor.

7. The sensor module of claim 1, further comprising a supply unit, in the second flow channel downstream from the first filter, configured to supply the reference fluid to the sensor.

8. The sensor module of claim 1, further comprising a first regenerative mechanism capable of regenerating a function of the first filter to reduce the amount of the first component.

9. The sensor module of claim 1, further comprising a second regenerative mechanism capable of regenerating a function of the second filter to reduce the amount of the second component.

10. A detection method comprising:
preparing a sensor module comprising a first supply unit provided in a first flow channel, a second supply unit provided in a second flow channel including a first filter configured to reduce an amount of a first component and the amount of the second component, a sensor, and a chamber in which the sensor is provided;
driving the first supply unit to supply a sample fluid to the sensor through the first flow channel;
driving the second supply unit to supply a reference fluid to the sensor through the second flow channel, the reference fluid including a second component that is included in the sample fluid and differs from the first component;
detecting the first component with the sensor;
controlling the first supply unit and the second supply unit such that the sample fluid from the first flow channel and the reference fluid from the second flow channel are supplied alternately to the chamber;
calculating concentration of the first component in the sample fluid on the basis of difference between a signal corresponding to a fluid yielded by reducing the second component in the sample fluid and a signal corresponding to a fluid yielded by reducing the second component and the first component in the reference fluid, which are received from the sensor, wherein the first flow channel and the second flow channel each comprise a second filter configured to reduce an amount of the second component; and the sensor module includes a third flow channel configured to discharge the sample fluid and the reference fluid after passing the sensor.

11. The detection method of claim 10, wherein the second filter is configured to reduce the amount of the second component more than the first component.

* * * * *